(12) United States Patent
Lu et al.

(10) Patent No.: US 10,710,759 B2
(45) Date of Patent: Jul. 14, 2020

(54) PACKAGING METHOD TO ENABLE RE-STERILIZATION OF MEDICAL DEVICE

(71) Applicant: Becton, Dickinson and Company, Franklin Lakes, NJ (US)

(72) Inventors: Di Lu, Ridgewood, NJ (US); Adam Zerda, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/414,131

(22) Filed: May 16, 2019

(65) Prior Publication Data
US 2019/0270533 A1 Sep. 5, 2019

Related U.S. Application Data

(63) Continuation of application No. 15/164,269, filed on May 25, 2016, now Pat. No. 10,293,965.
(Continued)

(51) Int. Cl.
*A61L 2/08* (2006.01)
*B32B 3/00* (2006.01)
(Continued)

(52) U.S. Cl.
CPC .............. *B65B 55/14* (2013.01); *A61B 50/30* (2016.02); *A61L 2/07* (2013.01); *A61L 2/20* (2013.01);
(Continued)

(58) Field of Classification Search
CPC ...... A61B 19/026; A61B 50/30; B65D 41/32; B65D 51/1605; B65B 61/005
(Continued)

(56) References Cited

U.S. PATENT DOCUMENTS

| 3,472,369 A | 10/1969 | Schuster |
| 4,660,721 A | 4/1987 | Mykleby |
| 5,868,244 A | 2/1999 | Ivanov et al. |

FOREIGN PATENT DOCUMENTS

| DE | 102004027923 A1 | 12/2005 |
| EP | 1520795 A1 | 4/2005 |

(Continued)

OTHER PUBLICATIONS

PCT International Preliminary Report on Patentability in PCT/US2016/034280 dated Dec. 7, 2017, 11 pages.
(Continued)

*Primary Examiner* — Monzer R Chorbaji
(74) *Attorney, Agent, or Firm* — Servilla Whitney LLC

(57) ABSTRACT

A method of packaging pre-filled medical devices is disclosed. The method comprises producing a packaging having a front panel and a back panel defining a compartment capable of holding one or more medical devices wherein at least one of the front panel or top panel has a portion containing a gas permeable material while the remaining portion of the pouch is gas impermeable. This gas permeable material allows gas to pass through the material and contact the one or more articles contained within the compartment or allows gas to pass through the gas permeable material from the inside of the compartment to the outside of the container. Upon completion of sterilization, the pouch is sealed and the gas permeable portion is cut away leaving the sterilized medical device enclosed in a completely gas impermeable pouch.

10 Claims, 4 Drawing Sheets

Related U.S. Application Data

(60) Provisional application No. 62/166,766, filed on May 27, 2015.

(51) Int. Cl.
*B65D 73/00* (2006.01)
*B65B 41/18* (2006.01)
*B65B 55/14* (2006.01)
*B65B 7/02* (2006.01)
*B65B 55/18* (2006.01)
*B65B 61/00* (2006.01)
*A61B 50/30* (2016.01)
*A61L 2/07* (2006.01)
*A61L 2/20* (2006.01)

(52) U.S. Cl.
CPC .............. *B65B 7/02* (2013.01); *B65B 55/18* (2013.01); *B65B 61/005* (2013.01); *A61B 2050/318* (2016.02); *A61L 2202/18* (2013.01); *A61L 2202/21* (2013.01); *A61L 2202/24* (2013.01)

(58) Field of Classification Search
USPC .... 206/524.2, 484.1, 439, 528, 344; 53/170, 53/425, 429, 467; 422/1, 26, 28, 300; 428/57, 221
See application file for complete search history.

(56) References Cited

FOREIGN PATENT DOCUMENTS

| | | |
|---|---|---|
| JP | 2001219976 A | 8/2001 |
| WO | 99/32044 A1 | 7/1999 |
| WO | 2005073091 A2 | 8/2005 |
| WO | 2007047028 A1 | 4/2007 |
| WO | WO 2007/047028 A1 * 4/2007 | ............... A61F 2/00 |

OTHER PUBLICATIONS

PCT International Search Report and Written Opinion in PCT/US2016/034280 dated Dec. 6, 2016, 17 pages.

\* cited by examiner

PACKAGING METHOD TO ENABLE RE-STERILIZATION OF MEDICAL DEVICE

CROSS-REFERENCE TO RELATED APPLICATIONS

This application is a continuation of U.S. patent application Ser. No. 15/164,269, filed on May 25, 2016, issued as U.S. Pat. No. 10,293,965 on May 21, 2019, which claims priority under 35 U.S.C. § 119(e) to U.S. Provisional Application No. 62/166,766, filed May 27, 2015, the disclosures of which are incorporated herein by reference in their entirety.

TECHNICAL FIELD

The present invention relates to method of packaging medical devices, and more particularly to a method of packaging pre-filled syringe for use in I.V. flush procedures.

BACKGROUND

Clean or sterile articles particularly useful for medical applications are packaged to preserve their sterility. The packaging for these articles is intended to provide a barrier to prevent contaminants, including microorganisms, from entering inside the packaging.

Many medical procedures require multiple components including medication and medical devices which must be collected by the clinician prior to beginning the procedure. The practice of assembling multiple components in advance of a procedure is known as "kitting" and many hospitals and independent companies provide a service by assembling these components and preparing them for use in medical procedures.

Drugs or other injectable/infusible solutions which are packaged in gas-permeable containers such as plastic ampoules, drug vials with rubber stoppers, IV solution bags, IV solution pouches and pre-filled flush syringes are commonly used in medical procedures and may be included in procedure kits. In many instances, the plastic ampoules, drug vials with rubber stoppers, IV solution bags, IV solution pouches and pre-filled syringe contains saline and other aqueous solutions. Ethylene oxide (EtO) sterilization is common methods used to prepare the kit for use in a sterile field. Currently, pre-filled saline syringes, plastic ampoules, drug vials with rubber stoppers, IV solution bags, IV solution pouches are packaged in gas permeable packaging which is also permeable to EtO gas, which is commonly used for sterilization of medical instruments. However, exposure of a plastic ampoules, drug vials with rubber stoppers, IV solution bags, IV solution pouches or pre-filled syringe to Ethylene Oxide (EtO) gas results in an undesirable effect of increasing the pH of the contents of the plastic ampoules, drug vials with rubber stoppers, IV solution bags, IV solution pouches or pre-filled syringe, e.g. saline. To overcome this undesired effect, the plastic ampoules, drug vials with rubber stoppers, IV solution bags, IV solution pouches or plastic pre-filled saline syringe is initially omitted from the medical procedure kit until after the other contents of the kit have been treated with Ethylene Oxide (EtO) gas. For some medical procedures, it is important to have sterile field ready plastic ampoules, drug vials with rubber stoppers, IV solution bags, IV solution pouches and/or pre-filled flush syringe which also could be sterilized following the assembly of the kit. Thus, there is a need for a packaged pre-filled flush syringe, plastic ampoules, drug vials with rubber stoppers, IV solution bags, IV solution pouches that are capable of withstanding EtO sterilization.

Therefore, there is a need for simple, straight forward easy-to manufacture medical device packaging method to provide sterile field ready and kit packable product.

SUMMARY

Aspects of the invention are directed to a method of packaging medical devices, and more particularly to a method of packaging pre-filled medical devices.

In a first aspect of the present invention, a method of packaging and sterilizing a chemically sensitive medical device is disclosed comprising: providing the medical device; providing a pouch having a non-permeable chamber and a gas-permeable header; placing the medical device in the pouch; sealing the pouch along the gas-permeable header, such that the non-permeable chamber remains accessible through the gas-permeable header; sterilizing the medical device with a sterilizing agent provided through the gas-permeable header to the non-permeable chamber; sealing the medical device in the non-permeable chamber within the pouch; and removing the gas permeable header resulting in a medical device packaged within the non-permeable chamber and sterilized.

In one or more embodiment of the present invention, the sterilizing agent is steam, heat, nitrous dioxide, or a combination thereof.

In one or more embodiment of the present invention, the gas impermeable portion of the pouch is made of a laminate of one or more plastic layers and aluminum foil.

In one or more embodiment of the present invention, the gas permeable header of the pouch is made of air permeable plastic film, paper or nonwoven.

In one or more embodiment of the present invention, the medical device comprises a plastic ampoule, drug vial with rubber stoppers, IV solution bag, IV solution pouch or pre-filled syringe. In a specific embodiment, the medical device is pre-filled with aqueous solution, a therapeutic agent or a combination thereof. In a very specific embodiment, the aqueous solution is saline.

In one or more embodiment of the present invention, the step of providing a pouch having a non-permeable chamber and a gas-permeable header is by flow wrapping.

In yet another embodiment, the step of providing a pouch having a non-permeable chamber and a gas-permeable header is by blister packing.

In yet another embodiment, the step of providing a pouch having a non-permeable chamber and a gas-permeable header is by 3-sided or 4-sided pouch.

In a second aspect of the present invention, a method of packaging and sterilizing a chemically sensitive medical device is disclosed comprising: providing a front panel comprising a first heat-sealable film having a gas permeable section attached to a separate gas-impermeable section, the front panel having a top edge, a bottom edge, and two side edges; providing a back panel comprising a second heat-sealable film having a gas permeable section attached to a separate gas-impermeable section, the back panel having a top edge, a bottom edge, and two side edges; aligning the gas permeable section of the front panel with the gas permeable section of the back panel; sealing the top edge, the bottom edge, and two side edges of the front panel to the bottom edge, and two side edges of the back panel to form an exterior pouch, the exterior pouch having a gas permeable section and a gas impermeable header section; placing one or more pre-filled medical devices in the gas-impermeable section of the pouch; sealing the film of the front panel to the film of the back panel in between the one or more medical device to create one or more interior three-sided individual chambers around the pre-filled medical device, each of the one or more three-sided individual chambers having an opening at the bottom of the gas permeable header section of the exterior pouch, the gas permeable header section being oriented on top of the openings and oriented parallel to two or more openings; performing sterilization on the exterior pouch; sealing along the opening of each of the one or more three-sided individual chambers located at the bottom of the gas permeable header section to form a second fully enclosed pouch around the pre-filled medical device, the second fully enclosed pouch having only gas-impermeable film; cutting the gas permeable section along a separation line to separate the second gas impermeable pouch.

In a third aspect of the present invention, a method of packaging and sterilizing a chemically sensitive medical device is disclosed comprising: providing a front panel comprising a first heat-sealable film having a gas permeable section attached to a separate gas-impermeable section, the front panel having a top edge, a bottom edge, and two side edges; providing a back panel comprising a second heat-sealable film having a gas permeable section attached to a separate gas-impermeable section, the back panel having a top edge, a bottom edge, and two side edges; aligning the gas permeable section of the front panel with the gas permeable section of the back panel; sealing the top edge, the bottom edge, and two side edges of the front panel to the bottom edge, and two side edges of the back panel to form an exterior pouch, the exterior pouch having a gas permeable section and a gas impermeable header section; placing one or more pre-filled medical devices in the gas-impermeable section of the pouch; sealing the film of the front panel to the film of the back panel in between the one or more medical device to create one or more interior three-sided individual chambers around the pre-filled medical device, each of the one or more three-sided individual chambers having an opening at the bottom of the gas permeable header section of the exterior pouch, the gas permeable header section being oriented on only one side of the openings; performing sterilization on the exterior pouch; sealing along the opening of each of the one or more three-sided individual chambers located at the bottom of the gas permeable header section to form a second fully enclosed pouch around the pre-filled medical device, the second fully enclosed pouch having only gas-impermeable film; cutting the gas permeable section along a separation line to separate the second gas impermeable pouch.

In a fourth aspect of the present invention, a method of packaging and sterilizing a chemically sensitive medical device is disclosed comprising: providing a front panel comprising a first heat-sealable film having a gas permeable section attached to a separate gas-impermeable section, the front panel having a top edge, a bottom edge, and two side edges; providing a back panel comprising a second heat-sealable film having a gas permeable section attached to a separate gas-impermeable section, the back panel having a top edge, a bottom edge, and two side edges; aligning the gas permeable section of the front panel with the gas permeable section of the back panel; sealing the top edge, the bottom edge, and two side edges of the front panel to the bottom edge, and two side edges of the back panel to form an exterior pouch, the exterior pouch having a gas permeable section and a gas impermeable header section; placing one or more pre-filled medical devices in the gas-impermeable section of the pouch; sealing the film of the front panel to the film of the back panel in between the one or more medical device to create one or more interior three-sided individual chambers around the pre-filled medical device, each of the one or more three-sided individual chambers having an opening at the bottom of the gas permeable header section of the exterior pouch, the gas permeable header section being interspersed between the gas impermeable section; performing sterilization on the exterior pouch; sealing along the opening of each of the one or more three-sided individual chambers located at the bottom of the gas permeable header section to form a second fully enclosed pouch around the pre-filled medical device, the second fully enclosed pouch having only gas-impermeable film; cutting the gas permeable section along a separation line to separate the second gas impermeable pouch.

In a fifth aspect of the present invention, a method of packaging and sterilizing a chemically sensitive medical device is disclosed comprising: providing a front panel comprising a first heat-sealable film having a gas permeable section attached to a separate gas-impermeable section, the front panel having a top edge, a bottom edge, and two side edges; providing a back panel comprising a second heat-sealable film having a gas permeable section attached to a separate gas-impermeable section, the back panel having a top edge, a bottom edge, and two side edges; aligning the gas permeable section of the front panel with the gas permeable section of the back panel; sealing the top edge, the bottom edge, and two side edges of the front panel to the bottom edge, and two side edges of the back panel to form an exterior pouch, the exterior pouch having a gas permeable section and a gas impermeable header section; placing one or more pre-filled medical devices in the gas-impermeable section of the pouch; sealing the film of the front panel to the film of the back panel in between the one or more medical device to create one or more interior three-sided individual chambers around the pre-filled medical device, each of the one or more three-sided individual chambers having an opening at the bottom of the gas permeable header section of the exterior pouch, the gas permeable header section being oriented above gas impermeable section; performing sterilization on the exterior pouch; sealing along the opening of each of the one or more three-sided individual chambers located at the bottom of the gas permeable header section to form a second fully enclosed pouch around the pre-filled medical device, the second fully enclosed pouch having only gas-impermeable film; cutting the gas permeable section along a separation line to separate the second gas impermeable pouch.

DETAILED DESCRIPTION

Figure 1:
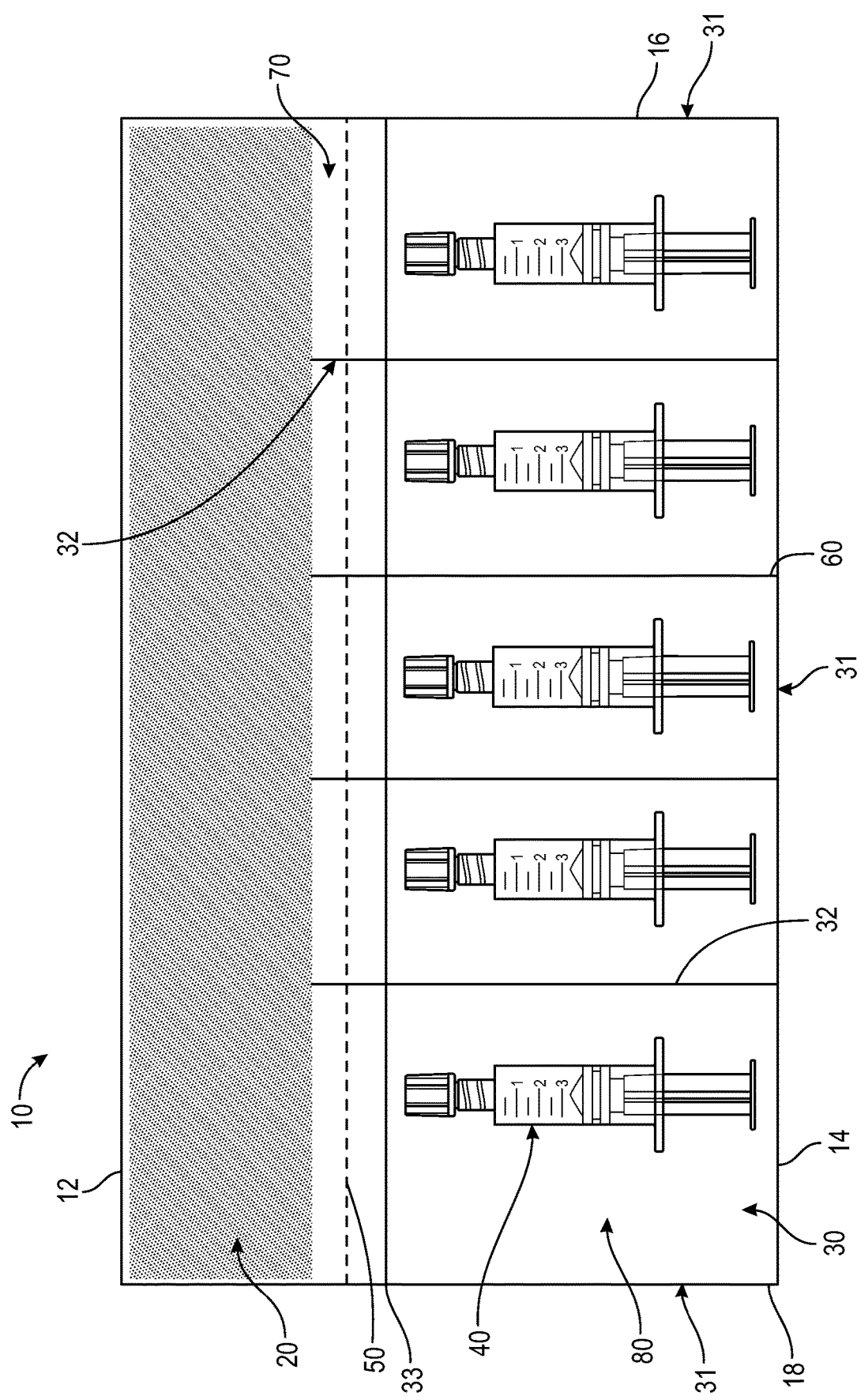
FIG. 1 is a perspective view of a sterilizable medical device package according to an embodiment of the present invention.

Before describing several exemplary embodiments of the invention, it is to be understood that the invention is not limited to the details of construction or process steps set forth in the following description. The invention is capable of other embodiments and of being practiced or being carried out in various ways.

With respect to terms used in this disclosure, the following definitions are provided.

As used herein, the terms "package" or "packaging" includes any material used to wrap or protect a medical device or product, such as plastic ampoules, drug vials with rubber stoppers, IV solution bags, IV solution pouches and syringes. Packaging can be rigid or flexible. Packaging includes, but is not limited to, medical packaging, pharmaceutical packaging, and child-resistant packaging. Medical and pharmaceutical packaging can include blister packs, flow wrap and 3 or 4 sided pouches.

As used herein, the terms "blister package" or "blister pack" includes several types of pre-formed packaging used for consumer goods, pharmaceuticals, medical devices, etc. The primary component of a blister pack is a cavity or pocket made from a formable web, usually a thermoformed plastic. The formable web can be rigid or flexible. The cavity or pocket is large enough to contain the good which is housed in the blister package. Depending on the application, a blister pack may have a backing of thermoformable material and a lidding seal of aluminum foil, paper, Tyvek®, plastic, or other medical grade materials. Blister packages can provide barrier protection from microorganisms and other contaminants, and can provide a certain degree of tamper resistance. The blister pack protects the pharmaceutical product from outside influences that would otherwise render it useless while allowing the manufacturer of the pharmaceutical product to package it using form-fill-seal equipment. The form-fill-seal process involves creating the blister pack from rolls of flat sheet or film, filling with the medical device or pharmaceutical product.

As used herein, the terms "flow wrap package" or "flow wrap pack" includes several types of pre-formed packaging used for consumer goods, pharmaceuticals, medical devices, etc. Flow wrapping is a packaging process that wraps a product with a film.

As used herein, the term "sterilization" refers to a wide variety of techniques employed to attenuate, kill or eliminate harmful or infectious agents. Examples of sterilization procedures include, for example, steam sterilization, ethylene oxide sterilization, gas plasma sterilization, ozone sterilization, hydrogen peroxide sterilization, heat sterilization, nitrous dioxide sterilization, or a combination thereof.

As used herein, the term "gas permeable" is intended to mean a material which will allow gas to pass through the material but does not allow airborne microbes, bacteria, viruses and mixtures thereof to pass through the material.

As used herein, "gas impermeable" is intended to mean a material which does not readily allow gas to pass through the material. In addition, the gas impermeable material also fails to allow airborne microbes, bacteria, viruses and mixtures thereof to pass through the material.

As used herein, the term "microorganism" refers to a microbe or organism that is unicellular or lives in a colony of cellular organisms. Microorganisms are very diverse; they include, but are not limited to bacteria, fungi, archaea, and protozoans.

In a first aspect of the present invention, a method is disclosed for using a heat-sealable film for packaging a pre-filled medical device, wherein the film includes a gas permeable section attached to a separate gas-impermeable section which allows for sterilization using steam, heat, nitrous dioxide, or a combination thereof. During manufacturing, the pre-filled medical devices are placed in the gas-impermeable section of the film and seals are used to create a first enclosed pouch. The first enclosed pouch comprising a gas permeable section and gas-impermeable section undergoes steam sterilization in an autoclave. In one or more embodiments, sterilization may also be by heat, nitrous dioxide, or a combination thereof. Following sterilization a final seal is performed, and the gas permeable section is cut and removed from the gas impermeable section to form a second enclosed package wherein the pre-filled medical device is fully enclosed in pouch consisting only of gas-impermeable film. Because the pre-filled medical device is fully enclosed in pouch consisting only of gas-impermeable film, the pouch containing the pre-filled medical device may be place in a kit that will undergo subsequent EtO sterilization without any adverse effects to the pre-filled medical device.

Thus, the present invention provides sterilizable packages that include a sheet material having a membrane through which steam, heat, nitrous dioxide, or a combination thereof, can be introduced into the interiors of the packages for sterilizing the contents of the package. The present invention also provides for sterilizable packages that are formed from the sheet material, and for processes of making such sterilizable packages. Thus, the present invention discloses an automated process for packaging that is capable of modifying a semipermeable container to become gas impermeable in a continuous manner and thus ready for EtO sterilization.

In one or more embodiments, the pouch can be prepared from two separate sheets of film material that are oriented in a face-to-face relation, and are sealed to each other along opposing edges to define a pouch having an interior space. In one embodiment the pouch is prepared by a first sheet of film material comprising both a gas permeable material and a gas impermeable section and a second sheet of film material comprising only a gas impermeable material. In another embodiment, both sheets of film material comprise a gas permeable material and a gas impermeable section.

Preferably, the inner surface of the sheet material comprises a heat sealable material. In the particular embodiment illustrated, the sheet material is made from a heat sealable material and the opposing ends of the pouch are sealed by producing a fusion bond or seal between contacting interior surfaces of the sheet material using pressure and heat or ultrasonic energy as is well known. Although referred to herein as "heat seals", it should be understood that this term is intended to apply both to seals formed by heating the contacting surfaces with a heated anvil or platen, as well as to heating and fusion produced by other methods, such as application of ultrasonic energy.

In one or more embodiments, one or more unsterilized prefilled medical devices are place on a first web of gas impermeable material. A second web of material having a gas permeable section is then placed over the first web of gas impermeable material. The first package is thereafter sealed.

The gas permeable section portion can comprise Tyvek® or other medical grade materials such as paper or flexible films. The sealed first package is permeable to steam, heat, nitrous dioxide, or a combination thereof, for sterilization but is impermeable to microorganisms. The gas permeable material may be composed of a material such as Tyvek®. Tyvek® is a synthetic material consisting of flashspun high-density polyethylene fibers (i.e. a spunbound olefin fiber). The material is lightweight and strong, and is resistant to tearing but can be cut with scissors or a knife. Water vapor and other gases can pass through Tyvek® as the material is highly, but, at the same time, the material is impermeable to liquid water and microorganisms. The material is permeable to the extent of allowing permeation of the material by sterilization gases or products.

Essentially any gas permeable material may be used in the present invention, provided that the material is permeable to a sterilizing gas but impermeable to airborne microbes, bacteria, viruses and mixtures thereof. Suitable gas permeable materials useable in the present invention include, for example, medical grade paper, nonwoven materials and other similar gas permeable materials.

The non-permeable material of the packaging can be made of a number of different materials, so long as the functionality of being non-permeable, or substantially non-permeable to EtO gas is maintained. For example, plastics, composites, metals, and other materials can provide this functionality.

In the present invention, suitable materials which may be used as the gas impermeable material include, for example, but are not limited to, polymeric plastic films, foils, fibrous webs and the like, laminates of one or more of these materials or a combination thereof of these materials. The gas impermeable material may be a single layer or a laminate of two or more layers.

It is also possible that the gas impermeable material is a laminate of a gas impermeable material and a gas permeable material. Examples of such laminates include, nonwoven/film laminates. These laminates may be beneficial to obtain a visibility to the inside of the product.

The package material can be made of a laminate of one or more plastic layers and a film of aluminum foil. The combined packaging material may be impermeable film comprising foil attached to a material Tyvek on one side or both sides.

The flexible web of the packaging can comprise plastic films such as flexible thermoform able plastics, including, but not limited to, nylon based films with polyethylene and ethyl vinyl acetate (EVA).

Suitable materials can be made from polymeric materials such as polyethylene, polypropylene, polyester, nylon, and the like, as well as any combination thereof. Plastic film materials include, for example, a low density polyethylene (LDPE) film, a LDPE/LLDPE (linear low density polyethylene) film laminate, a LDPE/MDPE (medium density polyethylene) film laminate, a LDPE/HDPE (high density polyethylene) film laminate, a ethylene-vinyl alcohol (EVOH) or the like. In addition, films made from a polyethylene/polypropylene combination may also be used. Films coated with metal coatings, also known as foils may also be used. In one embodiment of the present invention, the film materials used in the present invention include a polyolefin film, such as a polyethylene or polypropylene film. The thickness of the film can essentially be any thickness, provided that the film has sufficient EtO gas barrier property strength that the articles contained within the compartment of the pouch do not puncher or otherwise compromise the film or the pouch.

Referring to FIG. 1, in a first aspect of the present invention, a method is disclosed for a medical packaging 10, such as a pouch or blister, using a heat-sealable film for packaging a pre-filled medical device, wherein the film includes a gas permeable section 20 attached to a separate gas-impermeable section (30 which allows for sterilization using steam, heat, nitrous dioxide, or a combination thereof. The pouch 10 has a front panel and a back panel, each panel having a top edge 12, a bottom edge 14, two side edges 16, 18. During manufacturing, the front panel is directly or indirectly joined or connected to the back panel by having peripheral seals 31 create a completely enclosed exterior pouch 10 by sealing the respective top edge 12, bottom edge 14, and two side edges 16, 18 of the front panel to the respective top edge 12, bottom edge 14, and two side edges 16, 18 of the back panel. The front panel and back panel define a compartment capable of holding one or more medical device 40. At least one of the front panel or the back panel has a portion containing a gas permeable header section 20. The pre-filled medical device 40 are placed in the gas-impermeable section 30 of the film of and interior seals 32 are used to create an interior three-sided individual chamber around the pre-filled medical device 40 leaving an opening 70 toward the gas permeable header section 20. Thus, the gas impermeable section 30 may be divided into one or more individual chambers as defined by interior seals 32.

Thus the packaging interior is divided into a primary gas impermeable chamber comprising gas-impermeable section 30 and a gas permeable chamber comprising gas permeable header section 20. The gas permeable header section 20 can be implemented in a number of different structural embodiments, so long as the functional aspects of the header as described herein, including its permeability to the desired sterilization and inert gases, is maintained. The header can also be implemented as a patch, access point, or other gas-permeable implementation that performs in a similar manner as the header described herein with regard to the sterilization methodology of the present invention. The gas permeable header section 20 can be disposed at any location on the packaging that enables the method of sterilization.

Appropriate medical devices 40 for use with the present invention include surgical instruments, i.e., plastic ampoules, drug vials with rubber stoppers, IV solution bags, IV solution pouches or syringes, and any other medical device or instrument in need of sterilization. In addition, the pouch and interior three-sided individual chamber can be manufactured in any size and/or shape to contain any manner of medical device or instrument. The first enclosed pouch 10 comprising a gas permeable header section and gas-impermeable section undergoes steam sterilization in an autoclave. In one or more embodiments, sterilization may also be by heat, nitrous dioxide, or a combination thereof. Following sterilization, a final seal 33 is performed along opening 70 located at the bottom of gas permeable header section 20 to form a second enclosed package wherein the pre-filled medical device is fully enclosed in pouch consisting only of gas-impermeable film. The gas permeable section 20 is then cut and removed from the gas impermeable section by cutting along the separation line 50 to create a gas impermeable pouch 80. Because the pre-filled medical device is fully enclosed in pouch 80 consisting only of gas-impermeable film, the pouch containing the pre-filled medical device may be place in a kit that will undergo subsequent EtO sterilization without any adverse effects to the pre-filled medical device. As shown in FIG. 1, the gas permeable section 20 may be oriented to be on top of opening 70 and run parallel to two or more openings 70.

Figure 2:
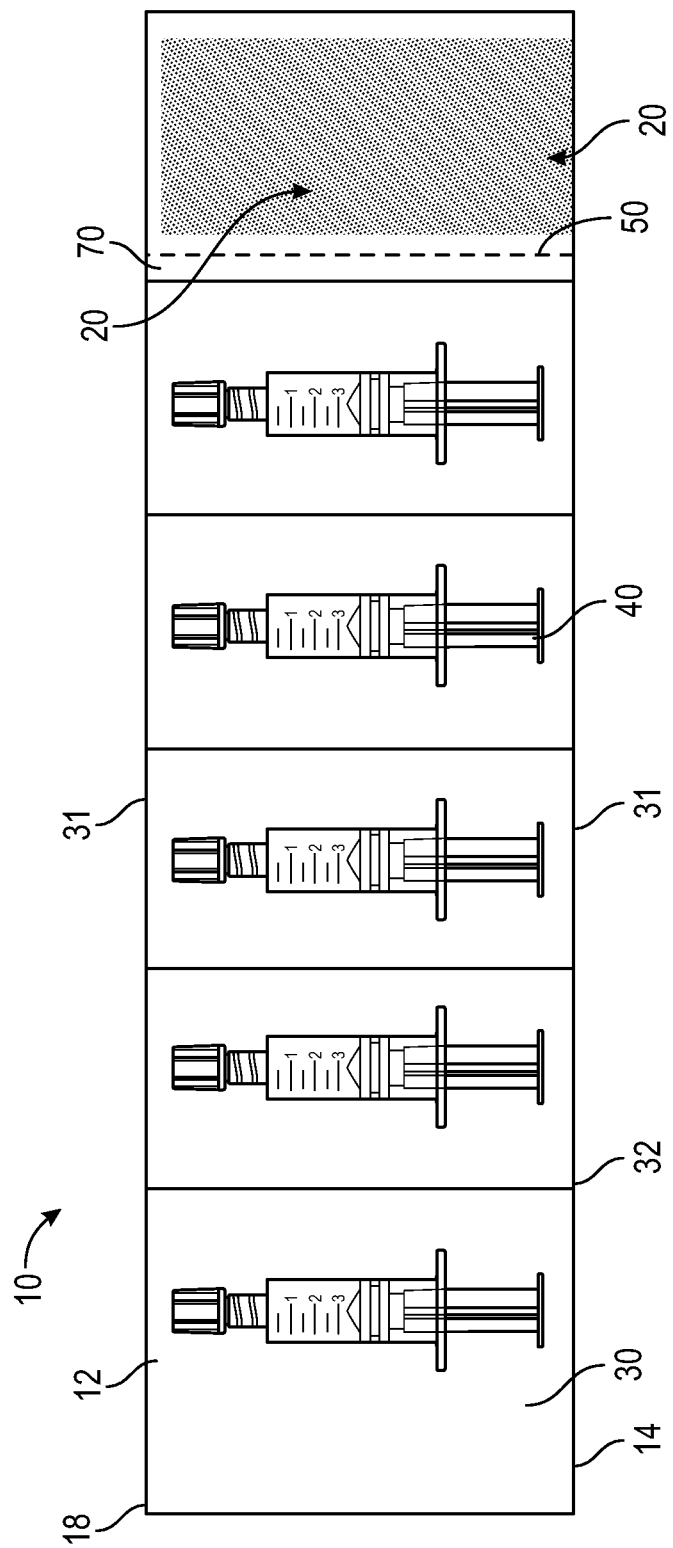
FIG. 2 is a top plan view of a medical device package according to an alternative embodiment of the present invention.

Referring to FIG. 2, in another embodiment of the present invention, a method is disclosed for a medical packaging, such as a pouch or blister, using a heat-sealable film for packaging a pre-filled medical device, wherein the film includes a gas permeable section 20 attached to a separate gas-impermeable section 30 which allows for sterilization using steam, heat, nitrous dioxide, or a combination thereof. During manufacturing, peripheral seals 31 are used to create a completely enclosed exterior pouch 10. The pre-filled medical devices 40 are placed in the gas-impermeable section 30 of the film. The first enclosed pouch comprising a gas permeable section and gas-impermeable section undergoes steam sterilization in an autoclave. In one or more embodiments, sterilization may also be by heat, nitrous dioxide, or a combination thereof. Following sterilization, interior seals 32 are used to create individual enclosures around the pre-filled medical devices 40 consisting only of gas-impermeable film. The gas permeable section 20 is then cut and removed from the gas impermeable section by cutting along the separation line 50. Because the pre-filled medical device is fully enclosed in second pouch 80 consisting only of gas-impermeable film, the pouch 80 containing the pre-filled medical device may be place in a kit that will undergo subsequent EtO sterilization without any adverse effects to the pre-filled medical device. As shown in FIG. 2, the gas permeable section 20 may be oriented on only one side of opening 70.

Figure 3:
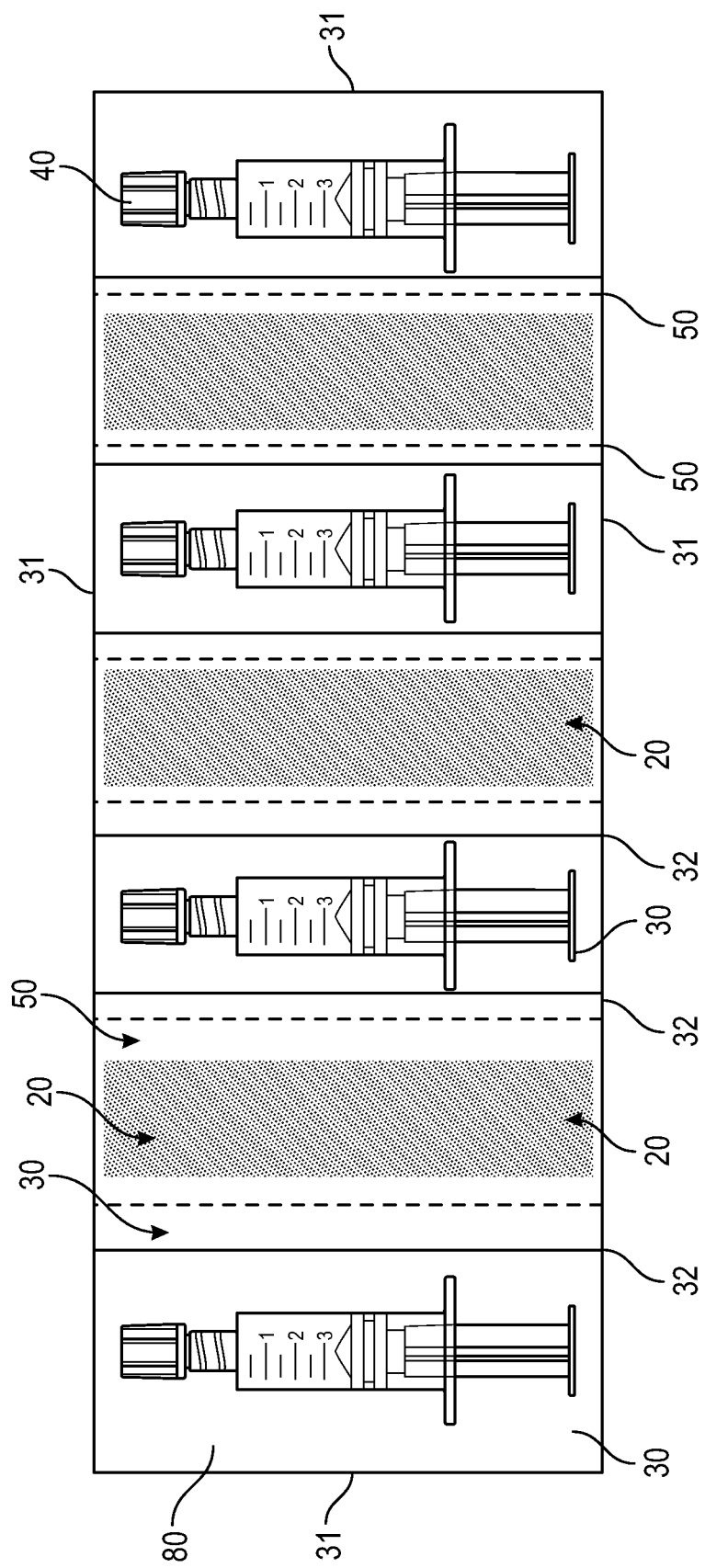
FIG. 3 is a top plan view of a medical device package according to another alternative embodiment of the present invention wherein a gas permeable section is interspersed between gas-impermeable sections.

Referring to FIG. 3, in yet another embodiment of the present invention, a method is disclosed for a medical packaging, such as a pouch, using a heat-sealable film for packaging a pre-filled medical device, wherein the film includes gas permeable sections 20 interspersed between gas-impermeable sections 30 which allow for sterilization using steam, heat, nitrous dioxide, or a combination thereof. During manufacturing, peripheral seals 31 are used to create a completely enclosed exterior pouch 10. The pre-filled medical devices 40 are placed in the gas-impermeable section 30 of the film. The first enclosed pouch 10 comprising a gas permeable section and gas-impermeable section undergoes steam sterilization in an autoclave. In one or more embodiments, sterilization may also be by heat, nitrous dioxide, or a combination thereof. Following sterilization, interior seals 32 are used to create individual enclosures around the pre-filled medical devices 40 consisting only of gas-impermeable film. The gas permeable sections 20 are then cut and removed from the gas impermeable section by cutting along the separation line 50. Because the pre-filled medical device 40 is fully enclosed in second pouch 80 consisting only of gas-impermeable film, the pouch containing the pre-filled medical device may be place in a kit that will undergo subsequent EtO sterilization without any adverse effects to the pre-filled medical device. As shown in FIG. 3, the gas permeable section 20 may interspersed between gas-impermeable sections 30.

Figure 4:
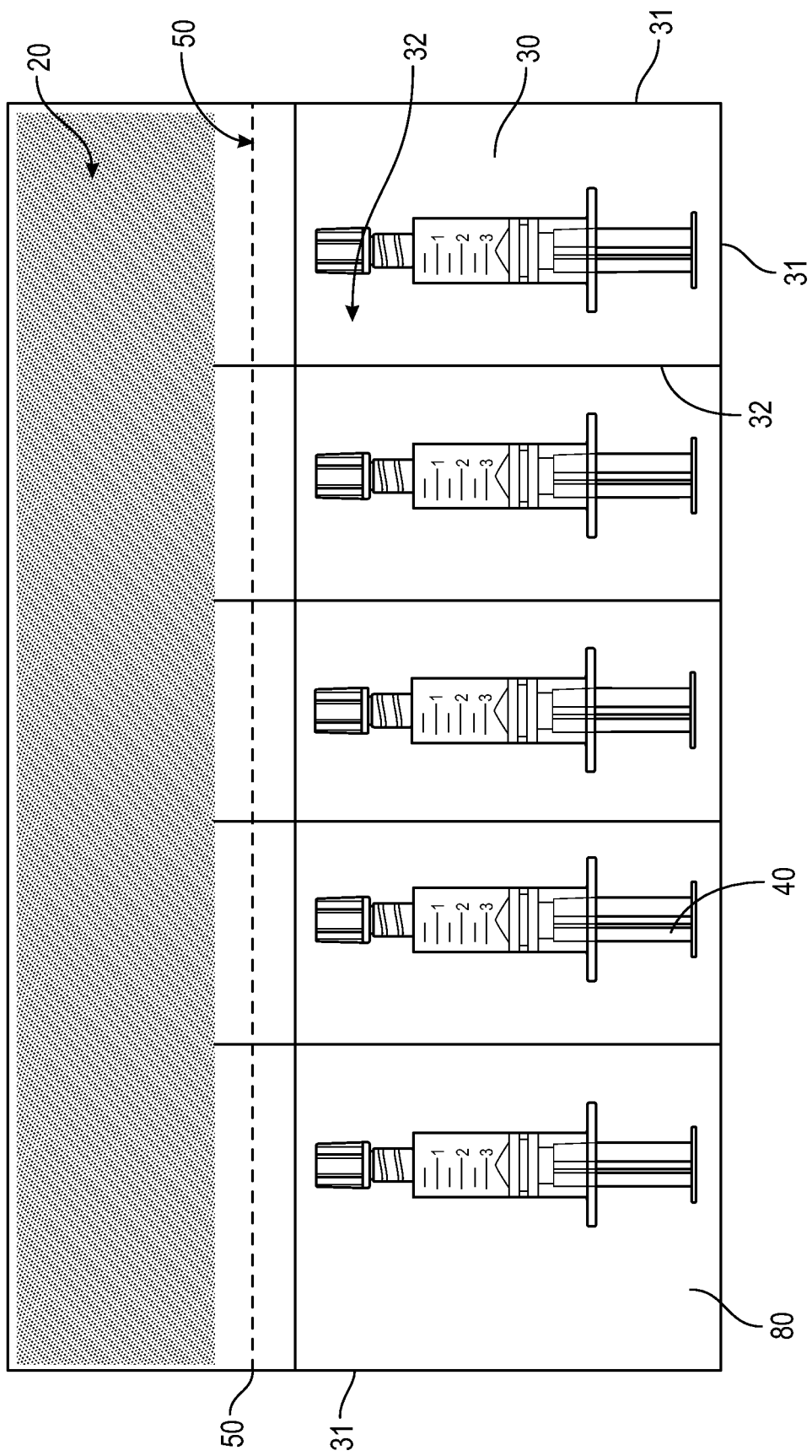
FIG. 4 is a top plan view of a medical device package according to another alternative embodiment of the present invention.

Referring to FIG. 4, in yet another embodiment of the present invention, a method is disclosed for a medical packaging, such as a pouch, using a heat-sealable film for packaging a pre-filled medical device, wherein the film includes a gas permeable section 20 attached to a separate gas-impermeable section 30 which allows for sterilization with steam, heat, nitrous dioxide, or a combination thereof. During manufacturing, peripheral seals 31 are used to create a completely enclosed exterior pouch 10. The pre-filled medical devices 40 are placed in the gas-impermeable section 30 of the film. The first enclosed pouch comprising a gas permeable section and gas-impermeable section undergoes steam sterilization in an autoclave. In one or more embodiments, sterilization may also be by heat, nitrous dioxide, or a combination thereof. Following sterilization, interior seals 32 are used to create individual enclosures around the pre-filled medical devices 40 such that the pre-filled medical device 40 is fully enclosed in pouch consisting only of gas-impermeable film. The gas permeable section 20 is then cut and removed from the gas impermeable section by cutting along the separation line 50. Because the pre-filled medical device is fully enclosed in pouch consisting only of gas-impermeable film, the pouch containing the pre-filled medical device may be place in a kit that will undergo subsequent EtO sterilization without any adverse effects to the pre-filled medical device. As shown in FIG. 4, the gas permeable section 20 may be oriented above gas impermeable section 30.

Thus, the present invention provides sterilizable packages that include a sheet material having a gas permeable membrane through which steam, heat, nitrous dioxide, or a combination thereof can be introduced into the interiors of the packages for sterilizing the contents of the package. The present invention also provides for sterilizable packages that are formed from the sheet material, and for processes of making such sterilizable packages. Thus, the present invention discloses a process for packaging that is capable of modifying a semipermeable container to become gas impermeable and thus ready for EtO sterilization.

As shown in FIGS. 1-4, the location, size and shape of the permeable section and the seal may be varied.

In one or more embodiments, the gas permeable section 20 may be incorporated into a gas permeable membrane that is formed from an opening in the sheet material which provides communication between the interior of the package and the surrounding environment. The gas permeable membrane comprises gas permeable section 20 that is disposed on a film sheet material. The gas permeable membrane may have a peripheral edge that overlies the film sheet material. The gas permeable section 20 may be joined to an inner or outer surface of the film sheet material. The gas permeable membrane may be joined to the film sheet material with a heat seal.

The gas permeable membrane is positioned on the sheet material, and hence the pouch, so that it is spaced away from the gas-impermeable section 30.

It should be understood that the size and location of the gas permeable membrane is not limited to any particular configuration and that the position and size can be selected to meet the particular requirements of the end user. Additionally, the position and size of the gas permeable membrane can be selected to optimize the sterilization process. In the figures, the sheet material is depicted as having a single gas permeable membrane having a generally rectangular shape. However, it should be recognized that the present invention is not limited to any particular number, shape or size of the gas permeable membrane and that the sheet material can include multiple gas permeable membranes of varying shapes and sizes.

In one or more embodiments, the type of packaging may be blister, flow wrap, 3 or 4 sided seal pouch.

In one or more embodiments, the present invention can be applied on either blister packaging or flow wrap packaging equipment for automated manufacturing.

In one or more embodiments, the material for the gas permeable section 20 may be paper or Tyvek which are able to survive the autoclave process.

In accordance with one aspect of the present invention, a desiccant, an antioxidant, an oxygen scavenger, an oxygen barrier or a combination thereof may be added to one or more individual chambers of gas impermeable chamber 30 before the pouch is sealed.

In one or more embodiments, the closing and sealing of exterior seal 31 and interior seal 32 can be by the application of a heat seal, mechanical engagement, adhesive engagement, etc. In addition, one of ordinary skill in the art will appreciate that the present invention is not limited with respect to the location of the seals, and the specific configuration illustrated and described herein. The seals can be configured and located in a number of different implementations, so long as the seals provide the functionality of sealing off a chamber that includes the gas-permeable area (e.g., header) and then subsequently sealing off the non-permeable material of packaging pouch so that the sterilized contents of the packaging pouch is maintained in its sterile environment.

The gas impermeable pouch 80 can be used as a "piggy-back" and be packed into a kit containing other articles which may be used in a surgical procedure. The medical device or articles placed in gas impermeable pouch 80 are such that they for one or other reasons must not be sterilized by gas of ethylene oxide and they are delivered in sterile packages. Gas impermeable pouch 80 may be thereafter brought together with a second package may be attached to the first package with the help of a tape or the like. All the disposable articles needed for the desired surgical procedure are thereby gathered to a single unit. If necessary, the combined package comprising gas impermeable pouch 80 may be subjected to subsequent ethylene oxide gas sterilization. Due to the impermeability to gas of ethylene oxide of primary gas impermeable chamber 80, the content of these packages will not be influenced by the subsequent sterilizing step.

According to one embodiment, the invention may be practiced with an automatic high-speed film wrapping system. The high-speed film wrapping system may include a feed conveyor, a film delivery unit, a wrapping station, a side seal assembly, an end sealer, conveyors and a heat shrink tunnel. The medical device to be wrapped in film may enter the system via a feed conveyor. The system wraps a medical device in a flexible plastic film in which the travel of the medical device is essentially continuous through the system in a feed direction. A conveyor may deliver the medical devices to a wrapping station in a spaced-apart and generally aligned pattern where a film from a film roll in a film delivery unit surrounds each medical device. The film enveloping each medical device is sealed at exterior seals 31 and interior seals 32 as described above by a side or end seal assembly to enclose the medical device with film. The film at the edge of the gas permeable section 20 may be severed and removed by a cutting head or cutting device. The film between the adjacent medical device is sealed and severed at the end sealer to produce individual sealed packages of the medical device.

The wrapped medical device may then be conveyed through a shrink or heat tunnel for shrinking of the film around the product. While a film delivery unit, wrapping station, end sealer and shrink tunnel are described herein as part of the system, specific models or embodiments of these and other components could readily be varied or changed as known by one of ordinary skill in this art without departing from the scope of this invention.

According to another embodiment, the invention may be practiced with an automatic high-speed blister pack system. In one embodiment, the thermoformed base web of a blister pack is made of a thicker gas impermeable plastic and cannot be collapsed, thus forming a solid backing. In another embodiment, the thermoformed base web of a blister pack is made of a gas impermeable plastic having a top portion that is gas permeable that forms a solid backing. The lidding film provides a peel-open feature that can be peeled open. The lidding film of a medical blister pack may porous to allow sterilization. Often, medical blister packs are made of Tyvek® or a similar medical grade material that is permeable to gases, but is not permeable to microorganisms. The lidding film can also be made of medical grade paper or a completely non-permeable film.

Blister packs can be created via thermoforming or cold forming. In the case of thermoforming, a plastic film or sheet is unwound from a reel and guided through a pre-heating station on the blister line. The temperature of the pre-heating plates is such that the plastic will soften and become pliable. The warm plastic then arrives in a forming station where a large pressure forms the blister cavity into a negative mold. The mold is cooled such that the plastic becomes firm again and maintains its shape when removed from the mold.

In the case of cold forming, an aluminum based-laminate film is simply pressed into a mold by means of a stamp. The aluminum elongates and maintains the formed shape. The use of aluminum offers a complete barrier for water and oxygen.

The thermoform able backing of the medical blister pack is generally comprised of a flexible thermoform able plastic film. The film is often multi-layered. The primary component is regularly a layer of approximately 15-30% Nylon, while the remaining layers can comprise substances including, but not limited to, polyethylene. The sealant layer can comprise, among others, ethyl vinyl acetate (EVA).

In one or more embodiments, the lidding film of a medical blister pack can be made from gas impermeable material. In another embodiment, the lidding film of a medical blister pack can be made from plastic, aluminum, or medical grade papers that are permeable to gases for sterilization but are impermeable to microorganisms. Most commonly, Tyvek® is used as a lidding material for medical blister packs.

Blister packs can be sealed in a variety of ways including, but not limited to, heat-sealing and cold sealing. Lidding materials can have a heat-seal coating applied to them; the lidding is then sealed to the backing using heat, which activates the coating. Blister packs can also be sealed using a cold seal process, which uses a combination of a pressure sensitive fold-over blister card and a transparent blister; the blister is trapped between two pieces of board that are bonded together under pressure without using any heat. Additionally, blister packs can be sealed by orienting multiple layers of film properly in order to make a seal.

In one or more embodiments, the blister pack comprising a gas permeable header section and gas-impermeable section undergoes steam sterilization in an autoclave. In one or more embodiments, sterilization may also be by heat, nitrous dioxide, or a combination thereof. Following sterilization, the gas permeable section of the backing is cut and removed from the gas impermeable section by cutting along a separation line to create a gas impermeable pouch. A gas impermeable lidding material is sealed to the backing creating a gas impermeable blister pack. Because the medical device, e.g. pre-filled syringe, plastic ampoule, drug vial with rubber stopper, IV solution bag, IV solution pouches, etc. is fully enclosed in pouch consisting only of gas-impermeable film, the pouch containing the pre-filled syringe may be place in a kit that will undergo subsequent EtO sterilization without any adverse effects to the pre-filled syringe.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as disclosed.

What is claimed is:

1. A method of packaging comprising:
   providing one or more pre-filled medical devices;

providing a pouch having a gas impermeable section divided into two or more individual gas impermeable chambers and a gas-permeable header;

placing each of the one or more pre-filled medical devices into the individual chambers of the gas impermeable section;

sealing the pouch along the gas-permeable header;

sterilizing the medical device with a sterilizing agent;

sealing each of the one or more pre-filled medical device into one or more of the individual chambers of the gas impermeable chamber; and removing the gas permeable header.

2. The method of claim 1, wherein the sterilizing agent is steam, heat, nitrous dioxide, or a combination thereof.

3. The method of claim 1, wherein the one or more gas impermeable chambers of the pouch is made of a laminate of one or more plastic layers and aluminum foil.

4. The method of claim 1, wherein the gas permeable header of the pouch is made of air permeable plastic film, paper or nonwoven.

5. The method of claim 1, wherein the medical device comprises a plastic ampoule, drug vial with rubber stopper, IV solution bag, IV solution pouch or pre-filled syringe.

6. The method of claim 5, wherein the medical device is filled with aqueous solution, a therapeutic agent or a combination thereof.

7. The method of claim 6, wherein the aqueous solution is saline.

8. The method of claim 1, wherein the step of providing a pouch having a gas impermeable section divided into two or more individual gas impermeable chambers and a gas-permeable header is by flow wrapping.

9. The method of claim 1, wherein the step of providing a pouch having a gas impermeable section divided into two or more individual gas impermeable chambers and a gas-permeable header is by blister packing.

10. The method of claim 1, wherein the step of providing a pouch having a gas impermeable section divided into two or more individual gas impermeable chambers and a gas-permeable header is by 3-sided or 4-sided pouch.

* * * * *